US007011092B2

(12) United States Patent
McCombs et al.

(10) Patent No.: US 7,011,092 B2
(45) Date of Patent: Mar. 14, 2006

(54) PORTABLE HYPOXIC APPARATUS

(75) Inventors: Norman R. McCombs, Tonawanda, NY (US); Michael R. Valvo, East Aurora, NY (US)

(73) Assignee: AirSep Corporation, Buffalo, NY (US)

(*) Notice: Subject to any disclaimer, the term of this patent is extended or adjusted under 35 U.S.C. 154(b) by 0 days.

(21) Appl. No.: 10/729,507

(22) Filed: Dec. 5, 2003

(65) Prior Publication Data

US 2004/0134493 A1    Jul. 15, 2004

Related U.S. Application Data

(60) Provisional application No. 60/432,913, filed on Dec. 12, 2002.

(51) Int. Cl.
 *A62B 19/00*    (2006.01)
(52) U.S. Cl. .............................. 128/205.12; 128/205.11; 128/205.27
(58) Field of Classification Search ........... 128/202.12, 128/205.11, 205.12, 205.27, 205.28, 205.26; 482/13
See application file for complete search history.

(56) References Cited

U.S. PATENT DOCUMENTS

| | | | | |
|---|---|---|---|---|
| 3,680,557 A | * | 8/1972 | Doniguian | 128/204.17 |
| 4,086,923 A | * | 5/1978 | Henkin | 128/205.11 |
| 4,802,899 A | * | 2/1989 | Vrana et al. | 96/109 |
| 5,101,819 A | * | 4/1992 | Lane | 128/204.18 |
| 5,207,623 A | * | 5/1993 | Tkatchouk et al. | 482/61 |
| 5,383,448 A | * | 1/1995 | Tkatchouk et al. | 128/205.11 |
| 5,531,807 A | * | 7/1996 | McCombs | 95/26 |
| 5,799,652 A |  | 9/1998 | Kotliar | |
| 5,850,833 A |  | 12/1998 | Kotliar | |
| 5,871,564 A | * | 2/1999 | McCombs | 95/98 |
| 5,924,419 A |  | 7/1999 | Kotliar | |
| 5,964,222 A |  | 10/1999 | Kotliar | |
| 5,988,161 A | * | 11/1999 | Kroll | 128/202.12 |
| 6,009,870 A | * | 1/2000 | Tkatchouk | 128/202.12 |
| 6,089,229 A | * | 7/2000 | Bathe et al. | 128/204.21 |
| 6,558,451 B1 | * | 5/2003 | McCombs et al. | 95/98 |
| 6,561,185 B1 | * | 5/2003 | Kroll | 128/202.12 |
| 6,565,624 B1 |  | 5/2003 | Kutt et al. | |
| 6,694,969 B1 | * | 2/2004 | Heinonen et al. | 128/200.24 |
| 6,701,923 B1 | * | 3/2004 | Cazenave et al. | 128/204.22 |
| 6,796,307 B1 | * | 9/2004 | Hughson et al. | 128/205.12 |
| 6,820,619 B1 | * | 11/2004 | Kroll | 128/205.11 |

OTHER PUBLICATIONS

NCBI website: Abstract of Journal of Applied Physiology article entitled "Living high-training low: effect of moderate-altitude acclimatization with low-altitude training on performance", by Levine et al., issued Jul. 1997, 1 page.
NCBI website: Abstract of Journal of Applied Physiology article entitled "Individual variation in response to altitude training" by Chapman et al., issued Oct. 1998, 1 page.
NCBI website: Abstract of International Journal of Sports Medicine article entitled "Training high-living low: changes of aerobic performance and muscle structure with training at simulated altitude", by Geiser et al., issued Nov. 2001, 1 page.

(Continued)

*Primary Examiner*—Mital Patel
(74) *Attorney, Agent, or Firm*—Hiscock & Barclay, LLP

(57) ABSTRACT

Hypoxic delivery apparatus producing from ambient air a product gas having a lower levels of oxygen concentration and delivering the product gas to a user of the apparatus in pulse doses. Alternatively, the apparatus may include a selector for alternately delivering either a nitrogen enriched gas or an oxygen enriched gas to the user.

14 Claims, 6 Drawing Sheets

OTHER PUBLICATIONS

NCBI website: Abstract of Advances in Experimental Medicine and Biology article entitled "Hypoxia training for sea-level performance. Training high-living low", by Hoppeler et al., issued 2001, 1 page.

NCBI website: Abstract of International Journal of Sports Medicine article entitled " Altitude and hypoxia training—a short review", by Boning, issued Nov. 1997, 1 page.

NCBI website: Abstract of Sports Medicine article entitled "Current trends in altitude training", by Wilber, issued 2001, 2 pages.

NCBI website: Abstract of Bulletin of Experimental Biology and Medicine article entitled "Adaption to hypoxia as a method of treatment and prevention of gastroduodenal mucosa lesions", by Agadzbanyan et al., issued Sep. 2001, 1 page.

NCBI website: Abstract of High Altitude Medicine & Biology article entitled "Intermittent hypoxia research in the former Soviet Union and the commonwealth of independent States: history and review of the concept and selected applications", by Serebrovskaya, issued Sep. 2002, 2 pages.

NCBI website: Abstract of Aviation, Space, and Environmental Medicine article entitled Improving athletic performance: is altitude residence or altitude training helpful?, by Fulco et al., issued Feb. 2000, 1 page.

NCBI website:Abstract of High Altitude Medicine & Biology article entitled "Intermittent hypoxic training: fact and fancy", by Levine, issued Summer 2002, 1 page.

NCBI website: Abstract of Journal of Applied Physiology article entitled "Living high-training low, altitude training improves sea level performance in male and female elite runners", by Stray-Gundersen et al., issued Sep. 2001, 1 page.

Schoene R.B. Hypoxic ventilatory response and exercise ventilation at sea level and high altitude. Chapter In: High Altitude and Man, Editor J.B. West, Waberly Press Inc., 1984, 11 pages.

Baker, A. & Hopkins, W.G. (1998). Altitude training for sea-level competition In: Sportscience Training & Technology, Internet Society for Sport Science. http://sportsci.org/traintech/altitude/wgh.html, 14 pages.

Journal of Applied Physiology article entitled "Cardiovascular response to hypoxia after endurance training at altitude and sea level and after detraining" by Katayama et al., issued Apr. 2000, 15 pages.

Abstract of Journal of Applied Physiology article entitled "Live-high, train low increases the hypoxic ventilatory response of well-trained endurance athletes", by Townsend et al., issued Jun. 2002, 2 pages.

GO2Altitude, Health and Fitness Equipment for Intermittent Hypoxic Training website, 2000, 4 pages.

Mar., 2002 News Relaese—AirSep's LifeStyle Portable Oxyge Concentrator Enters World Marketplace, 3 pages.

NCBI website: Abstract of High Altitude Medicine & Biology article entitled "Physiological effects of intermittent hypoxia", by Powell et al., issued Summer 2000, 1 page.

* cited by examiner

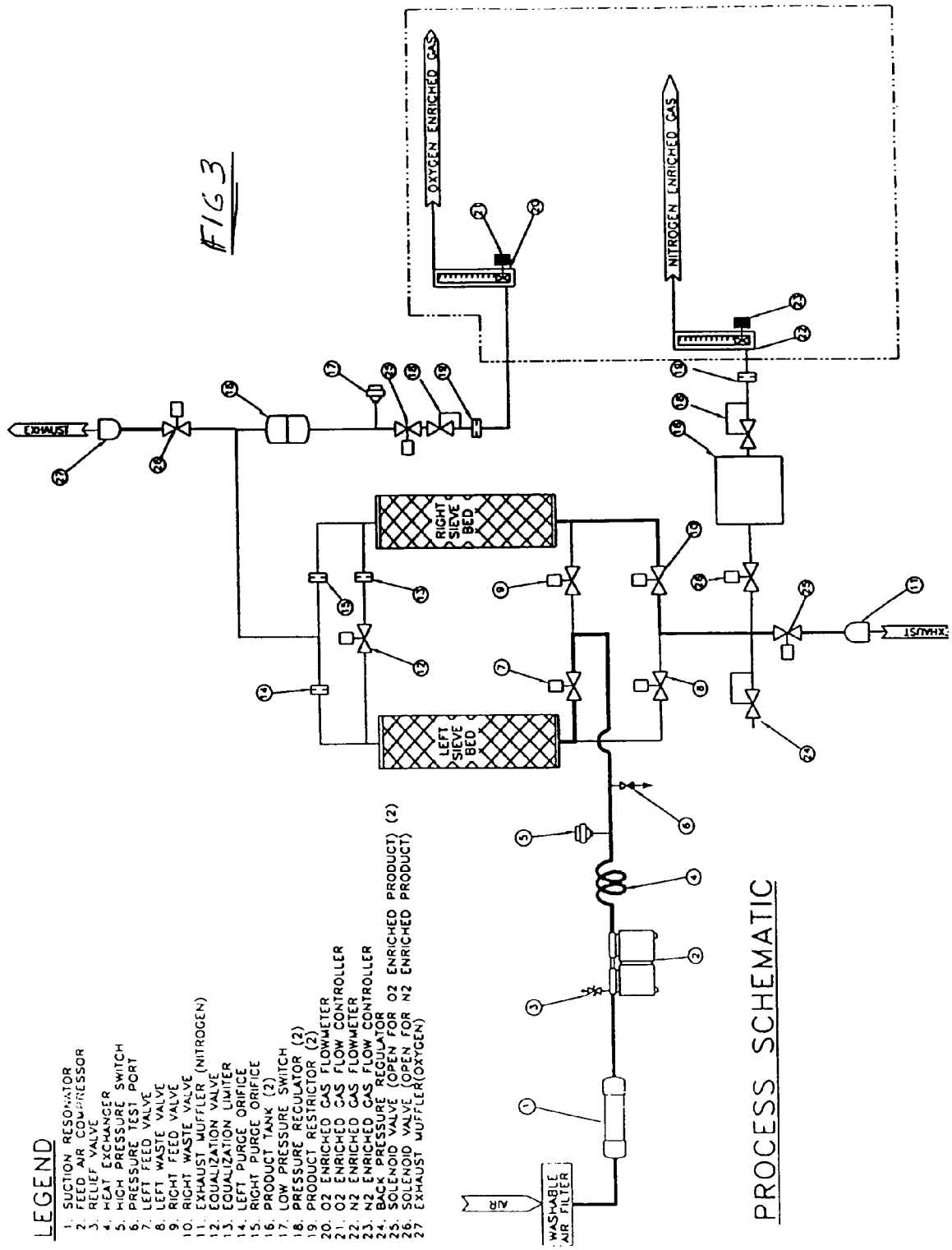

COMBINED PRODUCT OPTION

28. OXYGEN ENRICHED GAS CHECK VALVE
29. NITROGEN ENRICHED CHECK VALVE
30. PRODUCT FLOW METER
31. PRODUCT FLOW CONTROLLER

REP - Repressurize
DEP - Depressurize
Pressure [psig]

PORTABLE HYPOXIC APPARATUS

CROSS REFERENCE TO RELATED APPLICATIONS

This application claims priority from a Provisional Patent Application Ser. No. 60/432,913, filed Dec. 12, 2002.

FIELD OF THE INVENTION

This invention relates generally to apparatus for delivering reduced oxygen levels of a breathable gas for physical training purposes and/or for therapeutic use, by pressure swing adsorption ("PSA").

BACKGROUND OF THE INVENTION

The general benefits and value of conducting physical training in a hypoxic (oxygen-deprived or lower oxygen concentration than in normal air) environment are documented. For example, research in "Intermittent Hypoxic Training (IHT)" ranging from basic research (physiology, biochemistry, cell biology, etc.) to practical applications (athletic training, therapeutic applications) has been reported in a number of recognized, reputable journals appearing in the data base of the National Library of Medicine, including *High Altitude Medicine and Biology; Anesthesiology; Chest, Bulletin of Experimental Biology and Medicine, Sports Medicine; International Journal of Sports Medicine;* and *Journal of Applied Physiology.*

A significant portion of the research has dealt with the use of IHT for athletic training and conditioning, one studied training approach being the so called "living high—training low" approach. This approach involves having an athlete "live" in a hypoxic environment and undergo physical training in a normoxic environment. In multiple cited studies, this approach seems to have produced measurable improvement in athletic performance and, in some studies, measurable changes in physiological and biochemical/hematological parameters. While multiple authors state that more controlled research is needed to determine the total scope and value of the applicability of this type of training for athletes, the literature supports the basic idea as valid and useful.

From an athletic perspective, individuals who are trained under hypoxic conditions are expected to develop significantly improved physical endurance responses. These improved physical endurance responses are said to include both greater physical endurance at normal (low) altitudes (below 1800 meters above sea level), in such activities as distance running and swimming, and improved endurance at high altitudes (above 1800 meters) in such activities as mountain climbing.

Research is reported to have shown, for example, that hypoxic training resulting in acclimatization to a low oxygen environment can lead not only to increased endurance in that environment, but also lead to increased physiological and biochemical adaptation and defense mechanisms, including perhaps increased erythropoetin production (with possible increase in red blood cell production); improved immune system function; adrenal stimulation; cardiovascular adaptation (e.g., reduced peripheral resistance, increased vasodilation, and increased capillary density); decreased mean arterial blood pressure and decreased heart rate; and respiratory adaptation (e.g., increased pulmonary capacity, increased hypoxic ventilatory response, increased total lung capacity, increased vital lung capacity, and increased minute ventilation).

Controlled studies appear to have shown that athletes who have naturally occurring or congenital blunted ventilatory drives (i.e., less sensitivity and natural response to increased carbon dioxide and decreased oxygen levels in the blood) experience less dyspnea (i.e., subjective difficulty or distress in breathing or shortness of breath) and lower work of breathing at given levels of work, which may make exercise and athletic performance both more comfortable and more efficient. Such a blunted ventilatory drive may be one factor which predisposes certain individuals to outstanding athletic performance. It is postulated in the art that the equivalent of a natural blunted ventilatory drive can be achieved through physical training in a hypoxic environment, including the resulting benefits to endurance, athletic performance, and comfort and efficiency of exercise and athletic performance.

Studies also are reported to have shown that the changes produced by physical training in a hypoxic environment will decrease, even with continued physical training, in a normal-oxygen environment. The implication is that sustained hypoxic training is necessary to retain the benefits of hypoxic training.

While there apparently are significantly fewer references regarding therapeutic uses of IHT, several abstracts located cover the therapeutic uses of IHT, including the use of IHT to treat lesions of the gastroduodenal mucosa (ulcers) and the use of IHT to prevent refractory hypoxemia during chest surgery. Although we have no direct evidence to support any such benefits, it has also been said that hypoxic training may possibly provide increased resistance to ionizing radiation; improved resistance to poisons and venoms; improved resistance to viral infections; decreased recovery time after surgery; increased (improved) exercise till exhaustion (ETE) time; protection of the brain from oxidative stress; increased positive benefits from adaptive sleep; and improvements in a number of classes of diseases (e.g., ischemic heart disease, hypertension, bronchitis and asthma, gastric and duodenal ulcer disease, liver and pancreatic disease including diabetes, motor diseases and gynecological diseases.

In summary, studies known in the art appear to have established that physical training in a hypoxic (lower-than-normal oxygen concentration) environment can produce beneficial changes in biochemical and physiological functioning of the body, can produce beneficial improvement in and resistance to certain disease processes, and can produce beneficial improvement in athletic performance and endurance.

The many potential benefits of, and the wide range of potential uses and applications of, hypoxic environment physical training point to the value of developing hypoxic environment training methods and devices which are practical, cost effective, portable, and flexible.

The oldest and most direct method of hypoxic environment training is to have individuals or teams train at high altitudes, e.g., 1500 meters and higher. The cost, inconvenience, and danger from the environment, along with the lack of flexibility for the "high-low" approach (other than by moving up and/or down a mountain) make this an impractical method of hypoxic environment training in most cases. More accepted methods of hypoxic environment training now include sealed chambers or tents, and breathing masks used with pressurized tanks of low concentration oxygen or with pressure swing adsorption apparatus to produce a hypoxic gas. These methods allow flexibility in the composition of the breathing gasses delivered to trainees (adjusting the composition with more nitrogen and less oxygen for more hypoxic conditions) based primarily on the time that the user is in the hypoxic environment or breathes the hypoxic gas.

The isolation chamber and the tent both have the drawback of lack of mobility; the user must be stationary, within the sealed chamber or tent, and must travel to the location of the chamber or tent for each hypoxic training session. On the other hand, the use of a face mask, to which a regulated flow of hypoxic breathing gas is delivered, provides the user with some mobility during use, but still requires that the user be relatively stationary because of the relative size of the equipment. This forms the basis for the "high-low" approach to intermittent hypoxic training by exposure to hypoxic treatment for fixed periods of time, e.g., every 30 minutes for a prescribed amount of time within a predetermined training regimen. Thus, more vigorous motion or required exercise necessarily must stop or be significantly curtailed while the user is inhaling the hypoxic gases.

SUMMARY OF THE INVENTION

The present invention offers a very practical alternative to the known methods of intermittent hypoxic training by our invention of a highly portable apparatus that can enable the user to train both to the intermittent hypoxic training technique and to a continuous hypoxic training technique as with training at a high geographic altitude. Our portable system has great potential for use by athletes and possibly as well for therapeutic treatment as and when hypoxic therapeutic techniques become proven regimens for medical purposes.

The present invention comprises functional features which make it superior to other methods used for hypoxic training. The present invention is a gas concentration apparatus which separates gas mixtures by pressure swing adsorption (PSA), and more particularly for production of a product gas for breathing having a desired concentration and flow rate of a particular gas. Apparatus according to the present invention can be adjusted to produce particular nitrogen/oxygen gas ratios to simulate various geographic altitudes, and in one embodiment can also be switched immediately to produce a high concentration of oxygen if the user senses a level of exhaustion that requires an immediate "shot" of oxygen.

Moreover, the apparatus according to our invention is sufficiently light and portable to avoid the necessity of stopping physical activity while breathing the hypoxic gas. It can be fabricated in a small enough in size and light enough in weight to allow continuous use while the user is able to move about relatively unrestricted by the equipment. This is a great advantage which allows the user to train in all conceivable locations while performing physical tasks which relate directly to the athletic activity for which the user is in training. For example, a trainee could transport the present invention to a gym and use it continuously on a treadmill, a stair-climber, and/or any other training apparatus. For therapeutic medical uses, the present invention is very well suited to in-home, as well as clinic and hospital use, due to its portability and flexibility. It is even conceivable that the present invention can find a place in all manner of sports and athletic training, pilot training, diver training, and astronaut training.

Yet another distinct advantage of the present invention is its ability to be adjusted to deliver breathing gas to the user during only a portion of inspiration. It is known in the art that only the gas inhaled at the initial or effective stage of inhalation or inspiration is that which is usefully absorbed by the lungs. The remaining inhaled gas in the latter stage of inhalation is usually exhaled before it can be absorbed by the lungs. The kinetics of oxygen-carbon dioxide exchange in the pulmonary alveoli, along with the volume flow characteristics of human pulmonary inspiration, result in this phenomenon.

The present invention is adaptively flexible, so that it can actuate the flow of gas upon initial inhalation and terminate the flow of gas after the effective stage, say 190 ms after initial inhalation. It is thus possible to increase or decrease the effective flow rate of breathing the hypoxic gas by increasing or decreasing the activation time during each inhalation cycle. By delivering breathing gas only during the effective (initial) stage of inspiration, the present invention greatly increases the efficiency of the breathing gas delivered, resulting in requiring less breathing gas stored in tanks and/or produced by the adsorption process, allowing the apparatus to be smaller and lighter in weight (significantly more portable), and giving greater longevity to the apparatus and all its components, due to the need to produce less breathing gas for any given training session or therapeutic session while producing effective results.

Because of the great flexibility of the present invention, it can be adjusted to produce many concentrations of breathing gas. One advantage of this is to permit advancing a user through progressively greater degrees of hypoxia by producing breathing gasses with lower and lower percentages of oxygen during a series of training sessions.

Although the present invention can be used with a face mask with openings that allow inhalation of ambient air through openings in the mask, our preference is the use of a nasal-prong delivery device or cannula. A cannula minimizes encumbrance and interference by the device, while allowing for freer execution of training activities by the user.

We believe that use of the present invention will produce more efficient and faster results from all types of hypoxic training sessions, as well as allow efficient maintenance training sessions, e.g., to preserve the positive effects of the hypoxic training once achieved by the trainee. Because of the relative size, it can be used both in intermittent and continuous hypoxic training. We believe it may also be used for therapeutic purposes, for example, to enable persons with relatively weakened breathing abilities to strengthen their lung capacities.

Our invention uses a proven principle of pressure swing adsorption, or PSA. PSA apparatus and methods are described in the prior art. See U.S. Pat. Nos. 3,564,816; 3,636,679; 3,717,974; 4,802,899; 5,531,807 and 5,871,564, among others. For example, a pressure swing adsorption apparatus may include one or more adsorbers, each having a fixed sieve bed of adsorbent material to fractionate at least one constituent gas from a gaseous mixture by adsorption into the bed, when the gaseous mixture from a feed stream is sequentially directed through the adsorbers in a co-current direction. While one adsorber performs adsorption, another adsorber is simultaneously purged of its adsorbed constituent gas by part of the product gas that is withdrawn from the first or producing adsorber and directed through the other adsorber in a counter-current direction. Once the other adsorber is purged, the feed stream at a preset time is then directed to the other adsorber in the co-current direction, so that the other adsorber performs adsorption. The first adsorber then is purged either simultaneously, or in another timed sequence if there are more than two adsorbers, all of which is understood by those skilled in the art.

The invention uses a two or three bed PSA together with an integrated pulse dose delivery device or gas flow controller (GFC), as will be explained, with selectively variable effective oxygen/nitrogen breathing ratios to simulate different geographic altitudes. A further embodiment of the invention is selectable to deliver the reduced oxygen gas, or if desired by the user during or after physical training to switch to high oxygen levels to facilitate physical recovery.

BRIEF DESCRIPTION OF THE DRAWINGS

The features and advantages of the invention will become more apparent from a reading of the following description in connection with the accompanying drawing of a preferred embodiment of the invention, in which:

FIGS. 3 and 3A are schematic illustrations of a second embodiment of the invention, showing a combined PSA/GFC apparatus according to the invention that is selectable to deliver either a breathable gas with reduced oxygen levels or a breathable gas with a high concentration of oxygen.

DETAILED DESCRIPTION OF THE PREFERRED EMBODIMENT

Figure 1:
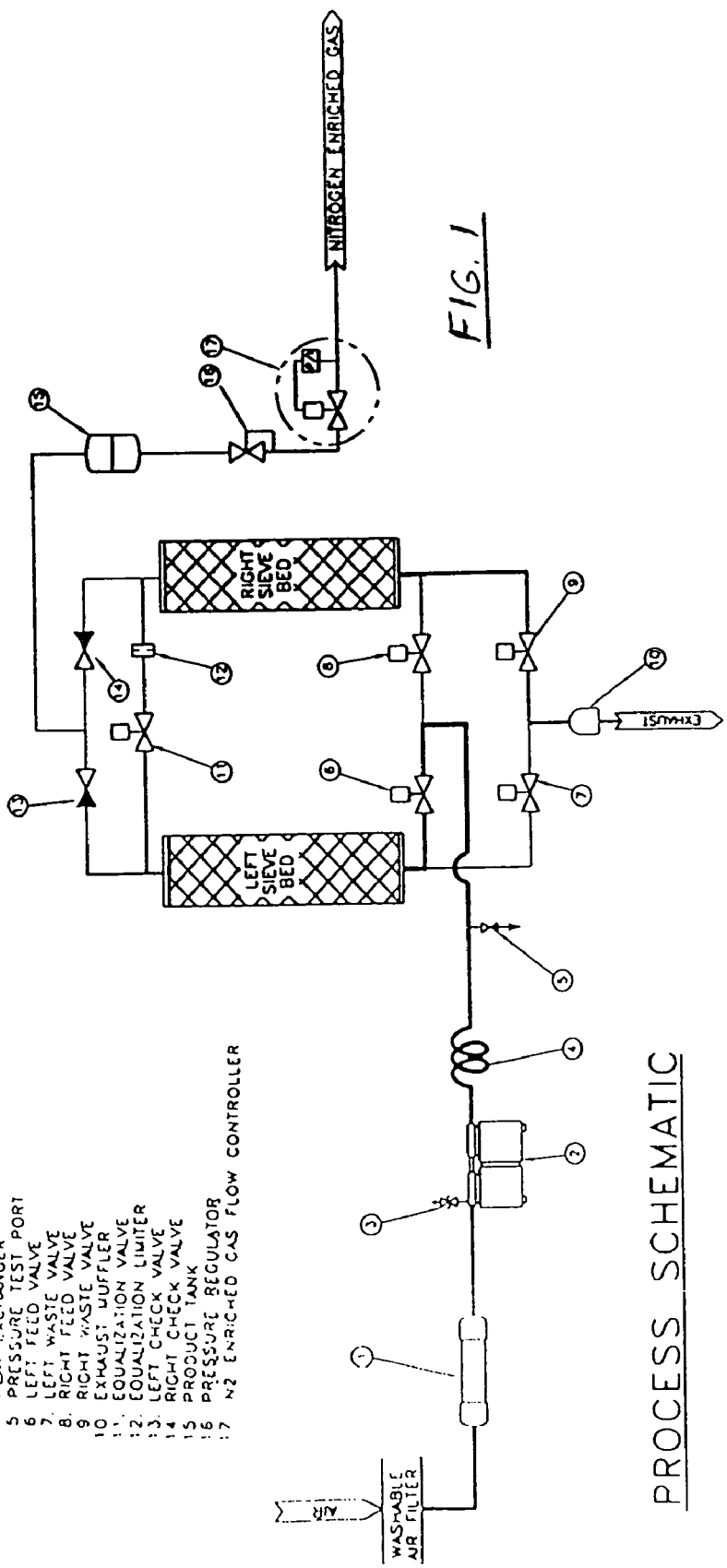
FIG. 1 is a schematic illustration of a combined PSA/GFC apparatus according to the invention to deliver a breathable gas with reduced oxygen levels.

Turning now to FIG. 1 of the drawing and in accordance with the present invention, there is shown a preferred embodiment, generally indicated as A, of a combined pressure swing adsorption apparatus and gas flow device, or PSA/GFC, used for fractionating at least one component, in this case oxygen, from ambient air, by pressure swing adsorption to produce a product gas with reduced oxygen concentration, and for delivering the product gas at specific and variable intervals upon demand by a user. The general operating principles of pressure swing adsorption are well known and are disclosed, for example, in commonly assigned U.S. Pat. Nos. 4,802,899, 5,531,807 and 5,871,564, the entire disclosures of which are incorporated by reference herein. Although these patents describe apparatus to produce product gases with higher oxygen concentrations, the principles of operation are similar, except that an oxygen adsorbent sieve material such as a known carbon molecular sieve material or synthetic zeolite is used in the embodiment of FIG. 1. In addition, conservation by pulse dosing of the supply of a product gas such as oxygen from a pressurized tank, in order to increase the useful life of the stored oxygen, also is generally known and is disclosed, for example in U.S. Pat. No. 6,427,690, issued Aug. 6, 2002 and entitled Combined Oxygen Regulator and Conservation Device, the entire disclosure of which is incorporated by reference herein. A combination apparatus for the delivery of higher concentrations of oxygen is described in co-pending U.S. Provisional Application No. 60/353,563 filed Jan. 31, 2002 and its corresponding non-provisional application Ser. No. 10/354,275, filed Jan. 30, 2003, both entitled Portable Oxygen Concentrator, the entire disclosures of which also are incorporated by reference herein.

With reference to FIG. 1, ambient air is supplied to the PSA/GFC apparatus A through a filtered intake and an intake resonator 1 to decrease the noise from the intake of the ambient air feed stream. The feed stream continues from resonator 1 and is moved from its outlet by a feed air compressor 2 and heat exchanger 4 alternatively to left and right adsorbers through feed valves 6 and 8 respectively.

When the feed stream alternatively enters the inlets at the lower ends of the adsorbers in a co-current direction, the respective adsorber fractionates the feed stream into the desired concentration of product gas. The adsorbent material used for the beds, if used to separate nitrogen from the ambient air, may be a sodium alumina silicate or other known adsorber material having equivalent properties.

In the embodiment of FIG. 1, unlike the apparatus described in the above mentioned PSA patents, oxygen rather than nitrogen is separated from the ambient air by using a known oxygen adsorbent sieve material such as a synthetic zeolite and is discharged to the atmosphere, whereas the balance of the ambient air forms product gas with a higher concentration of nitrogen for delivery to the user through the PSA/GFC in measured pulse doses.

The substantial or usable portion of the nitrogen enriched product gas generated by the ambient air flowing in the co-current direction sequentially in each one of the absorbers is directed through the respective outlet (at the upper ends) and check valve 13, 14 of the corresponding adsorber to a product manifold and then to a mixing tank 15. The balance of the product gas generated by each adsorber is timed to be diverted through a purge orifice 12 and a properly timed equalization valve 11 and an optional flow restrictor (not shown) to flow through the other adsorber in the counter-current direction from the respective outlet and to the respective inlet of the other adsorber to purge the adsorbed, primarily oxygen, gases. The counter-current product gas and purged gases then are discharged to the atmosphere from the adsorbers through properly timed waste valves 7, 9, tubing and a sound absorbing muffler 10.

The mixing tank 15 serves as a reservoir to equalize the enriched nitrogen product gas before delivery to the user through an apparatus outlet in the pulse dose mode, a piston-type pressure control regulator 16 to regulate the product gas pressure to be delivered to the user, a bacteria filter (not shown), and the gas flow controller or GFC 17 including the electronic control circuit and a flow control solenoid operated valve using the principles as disclosed in U.S. Pat. No. 6,427,690.

Figure 2:
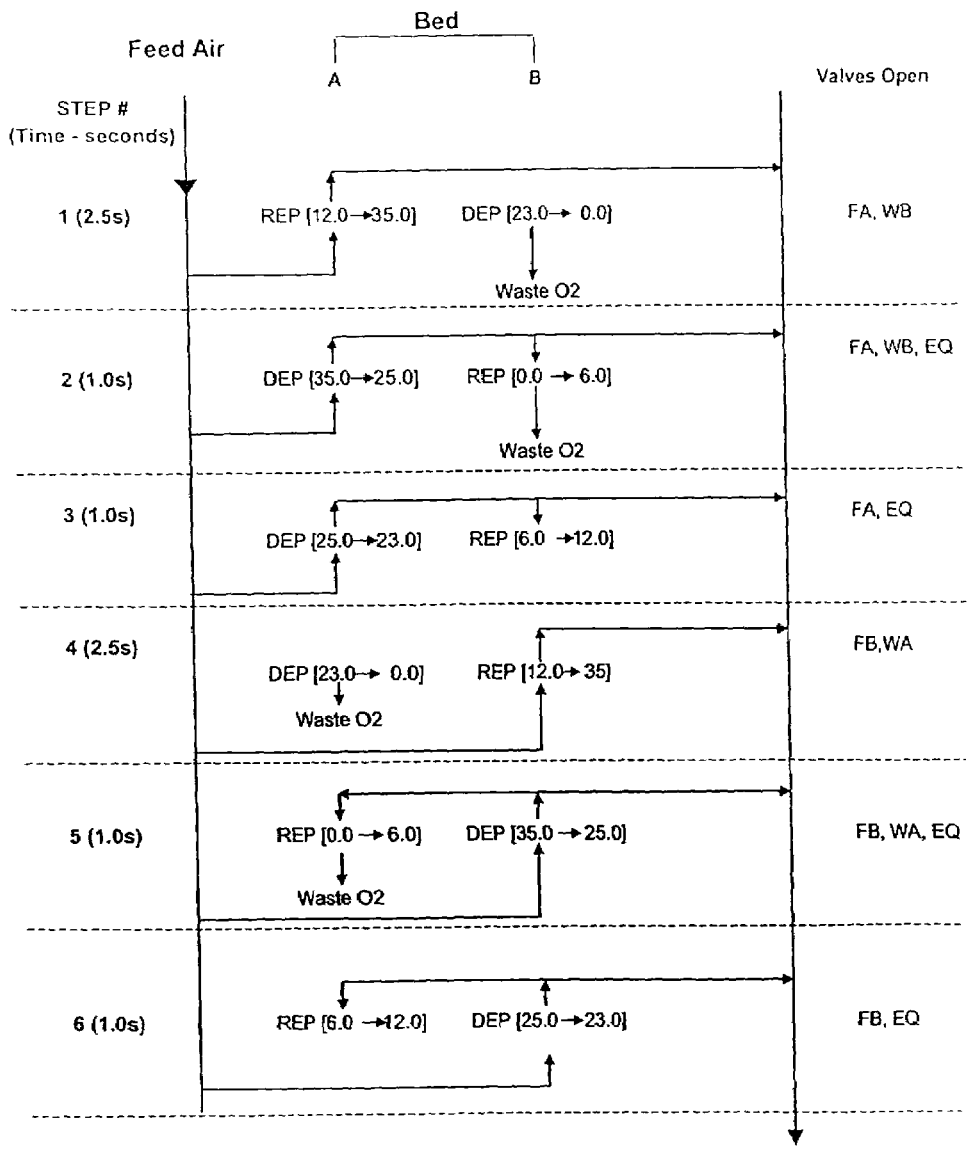
FIG. 2 is a flow chart illustrating a sequence of operation of the PSA/GFC apparatus.

FIG. 2 illustrates a flow diagram of the flow of gases by the timed sequence of the operating valves in which FA and FB are the feed valves 6 and 8 of the left or A bed and the right or B bed, respectively, WA and WB are the waste valves 7 and 9, respectively, and EQ is the equalization valve 11. The operational steps are timed in seconds, whereas the illustrated changes in pressure are measured as PSIG.

According to the invention, delivery of the PSA generated nitrogen enriched gas from the mixing tank 15 to the user is controlled by the GFC as will now be described.

As is noted above, the most effective use of inhaled gas occurs at the onset of inhalation. For example, various devices have been constructed to deliver oxygen from pressurized oxygen tanks only when inhalation is first sensed by the devices and only during the initial stage of the inhalation cycle. We have taken advantage of that well known principle to devise a much more compact and efficient PSA apparatus for the enriched nitrogen to deliver the enriched nitrogen at the initial stage of inhalation. As is disclosed in U.S. Pat. No. 6,427,690 and in co-pending applications Ser. No. 60/353,563 and No. 10/354,275, a low pressure sensor will detect a drop in pressure as sensed by inhalation of a user through a conventional cannula connected to the apparatus outlet by which the nitrogen enriched gas is delivered to the user. When the pressure sensor detects the pressure drop, the transducer circuitry in the electronic circuit causes the flow control valve in GFC 17 to be opened for a predetermined time and allow a predetermined amount of the enriched gas in the mixing tank 15 to be delivered to the user through the outlet. Depending on training and/or therapeutic levels required, the amount, concentration and timing of the delivered product gas is controlled by the electronic circuit using a programmable device for delivery of any one of a number of selectable effective flow rates and nitrogen concentrations, the settings for which may be made by a multiple position control switch.

In the second embodiment as shown in FIG. 3, the PSA/GFC may be switched from producing a high nitrogen concentration gas to one producing a high oxygen concentration product gas. In the embodiment shown in FIG. 3, the adsorbant sieve material is a conventional nitrogen adsorbing material, in which oxygen enriched gas is produced using the principles as described in co-pending U.S. application Ser. No. 09/851,750, now U.S. Pat. No. 6,558,451, issued May 6, 2003 and co-pending applications Ser. No. 60/353,563 and Ser. No. 10/354,275. When the apparatus is selected to produce a nitrogen enriched gas, a selector switch (not shown) simultaneously opens both valves 26 to exhaust the oxygen concentrated gas to the atmosphere and closes both valves 25 to cause the purged nitrogen gas to be delivered to the GFC 23 through its mixing tank 16, pressure regulator 18, flow restrictor 19 and flowmeter 22. On the other hand, if an oxygen enriched gas is desired, both valves 26 are closed and both valves 25 opened to exhaust the adsorbed nitrogen gas while causing the oxygen concentrated gas to be delivered to the GFC 21 through its corresponding mixing tank 16, its pressure regulator 18, flow restrictor 19 and flowmeter 20. As the flow rates and concentrations of the nitrogen and the oxygen concentrated gas when delivered to the user will differ, each is controlled by its own GFC timed to operate differently by the selector switches. The settings for delivering the oxygen concentrated gas may be scaled by effective oxygen concentrations, whereas the nitrogen delivery may be scaled by equivalent geographic altitudes. Suitable electronics to initiate and time flow can be made by those skilled in the art, referring for example, to the device shown in U.S. Pat. No. 6,427,690.

Figure 3A:
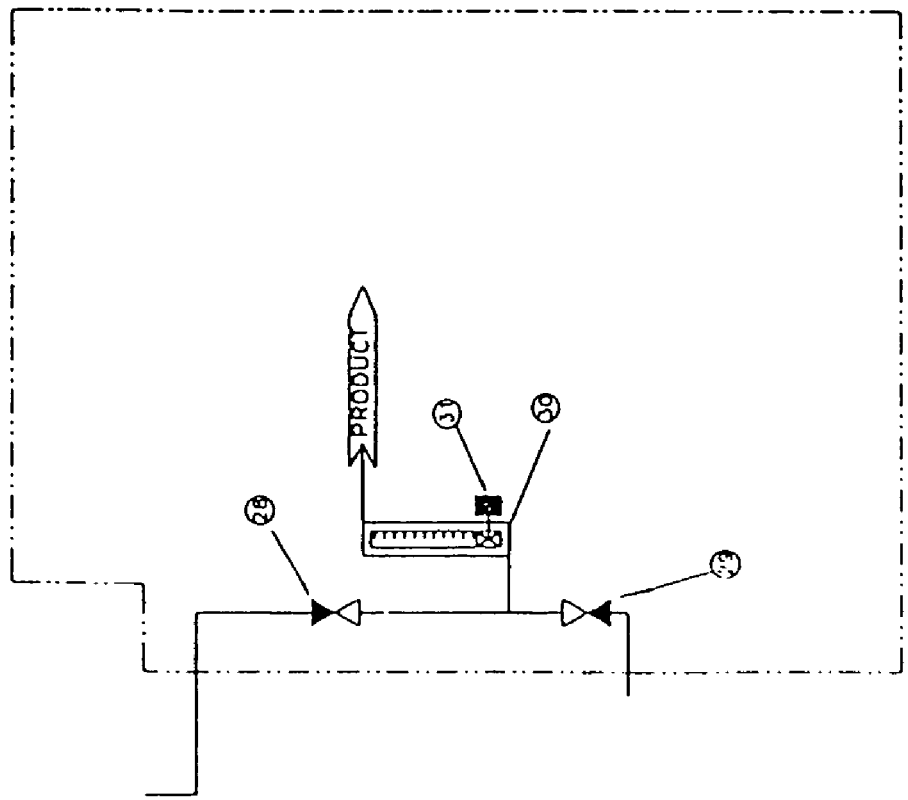

A variation of the second embodiment is shown in FIG. 3A, in which it is possible to incorporate the electronics of both of the GFCs into a single device with appropriate switch controls that could, for example, interchange the readable gas delivery scales when the function switch is changed between concentrated oxygen and concentrated nitrogen.

Figure 4:
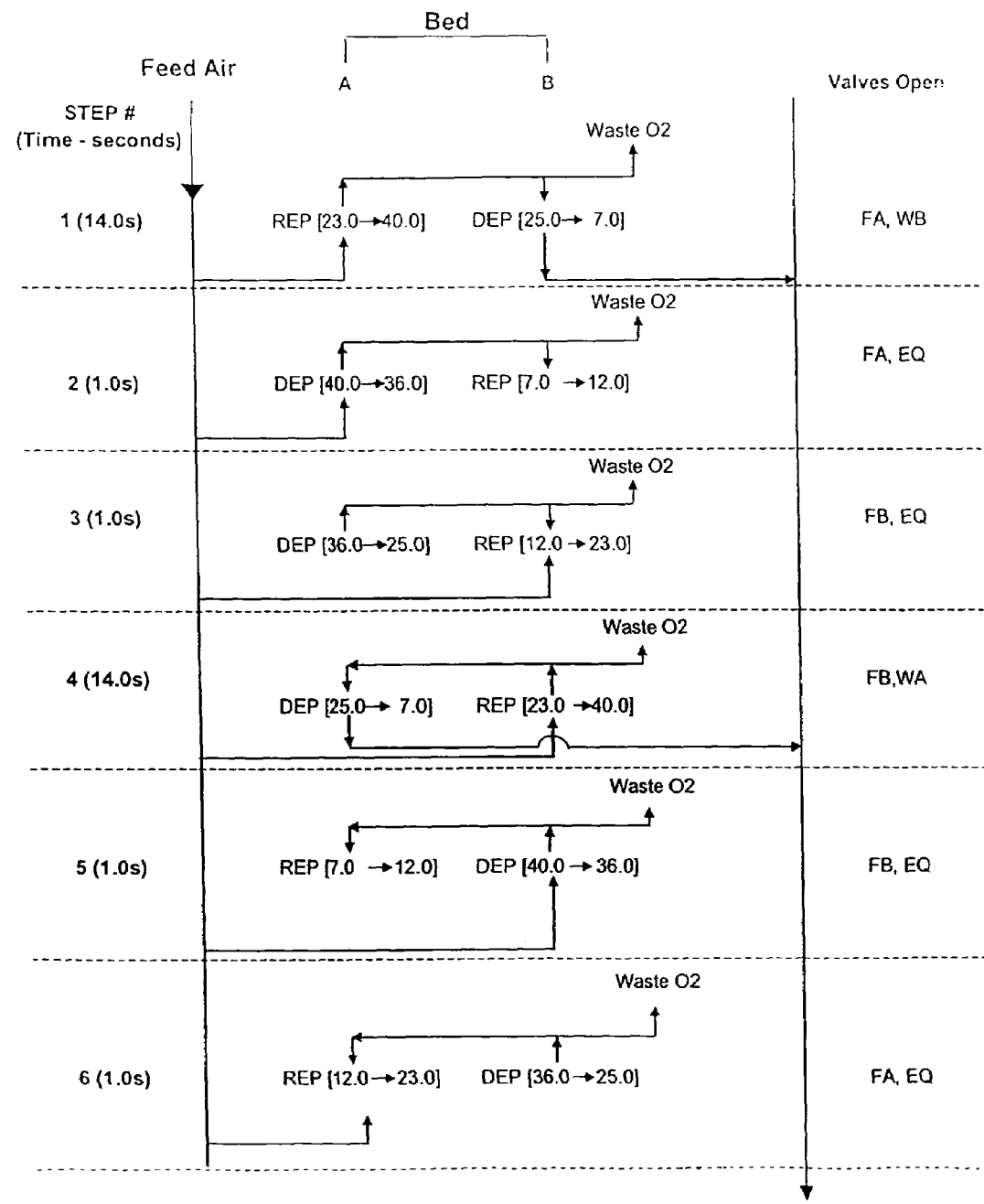
FIGS. 4 and 5 are flow charts illustrating the sequences of operation of the PSA/GFC apparatus according to the second embodiment.
Figure 5:
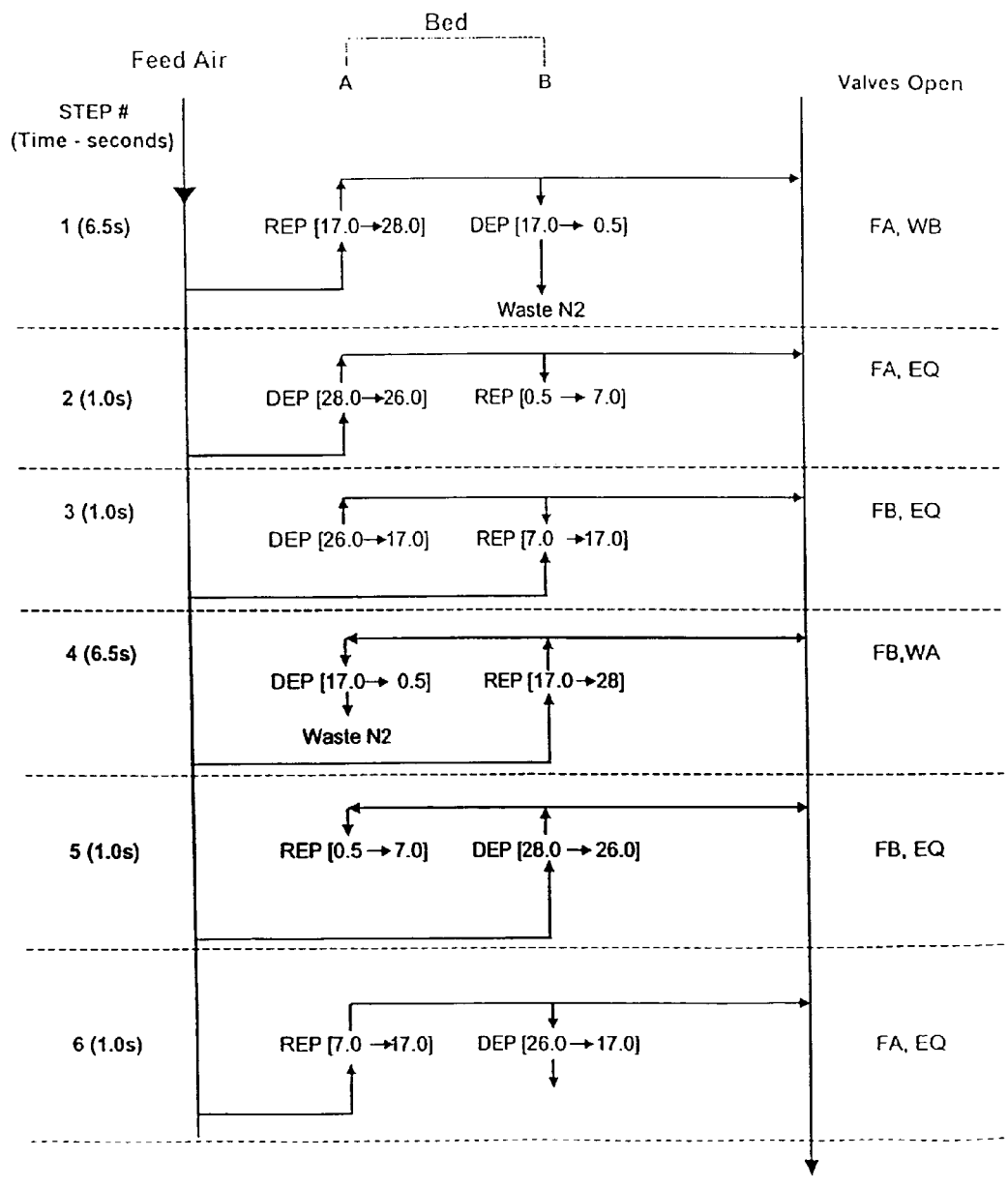

As with FIG. 2, FIGS. 4 and 5 illustrate the flow diagrams for the embodiment of FIGS. 3 and 3A, with the sequence and an example of timing of valves indicated according to whether a nitrogen enriched gas (FIG. 4) or an oxygen enriched gas (FIG. 5) is to be delivered to the user. It will be appreciated that the timing and operating parameters may be varied based on size of the components and the materials used.

Although the apparatus according to our invention is shown by two preferred embodiments, those skilled in the art will be able, from the description of our invention as herein provided, to produce a combined PSA/GFC apparatus, the individual fluid, electric and electronic components and controls of which can be found in the art or made by one skilled in the art following a reading of this description of the preferred embodiment. For portability, the apparatus may be made to be comparable in size and powered as in the LIFESTYLE™ Portable Oxygen Concentrator currently marketed by AirSep Corporation of Buffalo, N.Y. It is possible to use a three bed PSA as described in U.S. Pat. No. 6,558,451, the entire disclosure of which also is incorporated by reference herein, the use of which may not require a mixing tank because of the relatively constant output pressure achieved by a PSA made according to that invention. It also is possible to include a known gas monitor to measure the actual rather than the calculated concentration of the selected product gas being delivered to the user. In addition, those skilled in the art may be able to include other known monitor and/or safety features for use in monitored and/or unmonitored physical training or medical purposes, such as alarms to warn of excessive breathing rates causing "overdraw", a meter measuring use of the apparatus between servicing, a washable filter at the gas delivery outlet, and a test sequence circuit to ensure proper functioning of the apparatus.

To operate the apparatus the user accessible selector switch is turned to the desired "equivalent" flow rate on the operating panel both to turn on the PSA operation and to deliver nitrogen or oxygen enriched gas at the set altitude or rate. At start-up of the apparatus, all of valves are open to eliminate any back pressure and then either left open or closed in sequence through a timing mechanism of conventional switches and relay switches in the programmable circuit. As each of the feed, waste, and equalization valves is preferably a solenoid-type valve responsive to a turning on or shutting off of power to the valve, product-producing and regeneration operations are automatically controlled in the apparatus 20 by automatically controlling the amount of time that each of the feed, waste, and equalization valves are opened and closed.

The apparatus can be powered any one of three sources, including a rechargeable battery pack for active physical training, an AC adapter to connect the apparatus to an AC outlet for both rest periods and when using stationary training devices such as a treadmill, and a "cigarette lighter" adapter for a similar connection to an automobile type battery in a training vehicle. The circuit can be designed so that both the AC adapter and the automobile type battery can power the apparatus and recharge the battery pack simultaneously.

It will be understood that various modifications and substitutions may be made to the described embodiment without departing from the spirit of the invention. Accordingly, the described preferred embodiment is intended for purposes of illustration and not as a limitation.

What is claimed is:

1. A compact and portable hypoxic gas delivery apparatus by producing from ambient air a product gas having lower levels of oxygen concentration and delivering the product gas to a user of the apparatus, the apparatus comprising a pressure swing adsorption unit having at least one adsorber bed to receive ambient air and adsorb the nitrogen or the oxygen from the ambient air to produce both a nitrogen enriched gas and an oxygen enriched gas, and control means for delivering the nitrogen enriched gas in a pulse dose to a user for a selectable predetermined period of time and actuated upon initial inhalation by the user, the control means further comprising means for increasing or decreasing the effective flow rate of the nitrogen enriched gas by increasing or decreasing the activation time during each inhalation cycle.

2. The apparatus according to claim 1 and further comprising means for selectively switching the pressure swing adsorption unit to deliver in the pulse dose to the user the oxygen enriched gas instead of the nitrogen enriched gas.

3. The apparatus according to claim 1 in which the pressure swing adsorption unit comprises two adsorber beds alternately producing the enriched gases, and further comprising valve means for controlling the flow of air and gases alternately through the beds.

4. The apparatus according to claim 1 and further comprising means for adjusting the enrichment of the nitrogen in the nitrogen enriched gas to simulate various geographic altitudes.

5. The apparatus according to claim 1 and further comprising means for adjusting the enrichment of the nitrogen in the nitrogen enriched gas to produce selectively different concentrations of oxygen and nitrogen in the nitrogen enriched gas.

6. The apparatus according to claim 1 in which the pressure swing adsorption unit comprises three adsorber beds alternately producing the enriched gases.

7. The apparatus according to claim 1 and further comprising means for powering the apparatus from any one of three sources including a rechargeable battery pack, an AC adapter for connection to an AC outlet, and a DC adapter for connection to the power system of a vehicle.

8. A compact and portable hypoxic gas delivery apparatus by producing from ambient air a product gas having a lower levels of oxygen concentration and delivering the product gas to a user of the apparatus, the apparatus comprising a pressure swing adsorption unit having at least one adsorber bed to receive ambient air and adsorb the nitrogen or oxygen from the ambient air to produce both a nitrogen enriched gas and an oxygen enriched gas, and means for selectively delivering either the nitrogen enriched gas or the oxygen enriched gas to a user during inhalation by the user.

9. The apparatus according to claim 8 and further comprising means control means for delivering the selected enriched gas in pulse doses to the user at selectable rates and actuated upon initial inhalation by the user.

10. The apparatus according to claim 9 in which the control means actuating the flow of delivered gas upon initial inhalation further comprises means for increasing or decreasing the effective flow rate of the selected enriched gas by increasing or decreasing the activation time during each inhalation cycle.

11. The apparatus according to claim 8 in which the pressure swing adsorption unit comprises two adsorber beds alternately producing the enriched gases, and further comprising valve means for controlling the flow of air and gases alternately through the beds.

12. The apparatus according to claim 8 and further comprising means for adjusting the enrichment of the nitrogen in the nitrogen enriched gas to simulate various geographic altitudes.

13. The apparatus according to claim 8 and further comprising means for adjusting the enrichment of the nitrogen in the nitrogen enriched gas to produce selectively different concentrations of oxygen and nitrogen in the nitrogen enriched gas.

14. The apparatus according to claim 8 in which the pressure swing adsorption unit comprises three adsorber beds alternately producing the enriched gases.

* * * * *